United States Patent [19]

Suzuki et al.

[11] Patent Number: 4,824,952
[45] Date of Patent: Apr. 25, 1989

[54] ISOQUINOLINE DERIVATIVE

[75] Inventors: Tsuneji Suzuki, Kanagawa; Kunio Sannohe, Kanagawa; Toshihiko Ito, Kanagawa; Masahiko Maruyama, Chiba; Joji Kamiya, Chiba; Makoto Hirayama, Chiba; Takafumi Kitano, Chiba; Akira Awaya, Kanagawa, all of Japan

[73] Assignee: Mitsui Toatsu Chemicals, Inc., Tokyo, Japan

[21] Appl. No.: 754,286

[22] Filed: Jul. 12, 1985

[30] Foreign Application Priority Data

Jul. 26, 1984 [JP] Japan ................. 59-154108

[51] Int. Cl.$^4$ .................................. A61K 217/26
[52] U.S. Cl. ..................... 546/141; 546/15; 546/270; 546/334; 546/335; 549/336
[58] Field of Search ....................... 546/141

[56] References Cited

U.S. PATENT DOCUMENTS 4,260,763 4/1981 Bartmann et al. ............. 546/141
2352702 6/1975 Fed. Rep. of Germany .
270260 7/1978 Fed. Rep. of Germany .
WO/8400756 3/1984 PCT Int'l Appl. .

OTHER PUBLICATIONS

*Stedman's Medical Dictionary*, 24th ed., Williams & Wilkins, Baltimore, pp. 226-227.
Freedman, et al., "J. Org. Chem.," Vol. 33, No. 9, 1968, pp. 3648-3650.
*Monatsh. Chem.* 108(3), p. 691-692 (1977).
JOURNAL OF MEDICINAL CHEMISTRY, vol. 17, No. 12, January 1974, pages 1272-1276, American Chemical Society, Washington, D.C. US, A. Rosowsky et al., : Pyrimido [4,5-c] isoquinolines. 2. Synthesis and biological evaluation of some 6-alkyl-, 6-aral-kyl-, and 6-aryl-1,3-diamino-7,8,9,10-tetrahydropyrimido [4,5-c] isoquinolines as potential folate antagonists.
Yukhnevich et al., "Chemical Abstracts", vol. 80, 1974, col. 82596n.
Pastors, "Chemical Abstracts", vol. 85, 1976, col. 85:32778f.

Primary Examiner—Glennon H. Hollrah
Assistant Examiner—James H. Turnipseed
Attorney, Agent, or Firm—Browdy and Neimark

[57] ABSTRACT

An isoquinoline derivative of the following formula:

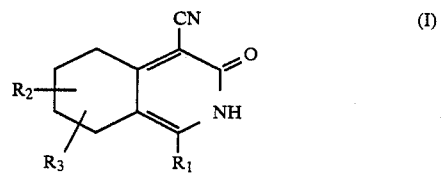

wherein $R_1$ is a methyl or a methoxymethyl group and $R_2$ and $R_3$ are each a hydrogen atom or a methyl, ethyl, methoxy, a cyclohexyl, a phenyl, a 3,4-dimethoxyphenyl, a pyridyl or an oxo (=O) group;

and therapeutically acceptable salts thereof which exhibit a low toxicity and a wide range of safety and are highly useful as a cardiotonic medication.

4 Claims, No Drawings

ISOQUINOLINE DERIVATIVE

FIELD OF THE INVENTION

This invention relates to a novel isoquinoline derivative and therapeutically acceptable salts thereof. This isoquinoline derivative and salts thereof are available as a cardiac.

BACKGROUND OF THE INVENTION

Digitalis preparations such as digoxin and digioxin have been conventionally used as cardiotonics in treating cardiac insufficiency (eee, e.g., Iyakuhin Yoran, pp. 324–327, 1977, Yakugyo Jiho Sha). While other cardiotonic compounds such as nicotinonitrile derivatives (see, e.g., Japanese patent Laid-Open No. 70868/1982), imidazolone derivatives (see, e.g., Japanese patent Laid-Open No. 155368/1984and dihydropyridazinone derivatives (see, e.g., Japanese patent Laid-Open No. 74679/1983) have been reported.

Digitalis preparations presently used in the above treatment have a very limited range of safety so that they should be handled by a skillful person. In addition, it has been reported that these preparations might exhibit some side effects including arrhythmia. On the other hand, the nicotinonitrile derivatives, imidazolone derivatives and dihydropyridazinone derivatives as recently reported have some disadvantages such as a low cardiotonic effect, a very limited range of safety, an effect of increasing myocardial rhythm or a high toxicity in animals.

SUMMARY OF THE INVENTION

We have studied to develop a compound having a wide range of safety without any side effects and consequently found that an isoquinoline derivative exhibits a high cardiotonic effect and a low toxicity, thus completing the present invention. The isoquinoline derivative of the present invention is a compound represented by the general formula:

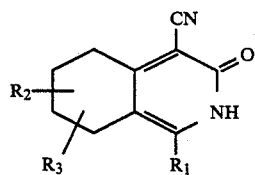

(I)

wherein $R_1$ is a methyl or a methoxymethyl group and $R_2$ and $R_3$ are each a hydrogen atom or a lower alkyl, a lower alkoxyl, a cyclohexyl, a phenyl, a substituted phenyl, a pyridyl or an oxo (=O) group, as well as therapeutically acceptable salts thereof. The compound (I) of the present invention may be present in the form of a tautomer of the formula:

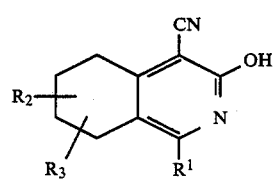

(II)

which is, of course, included in the present invention.

DETAILED DESCRIPTION OF THE INVENTION

The isoquinoline derivative of the present invention may be, for example, prepared in the following manner:

(1)

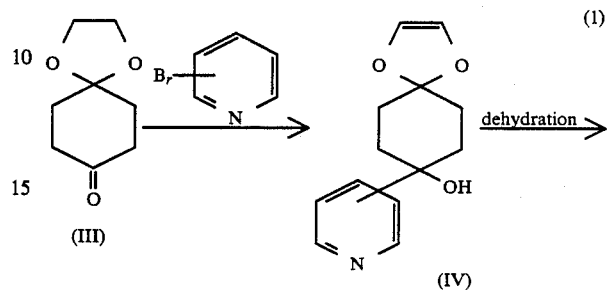

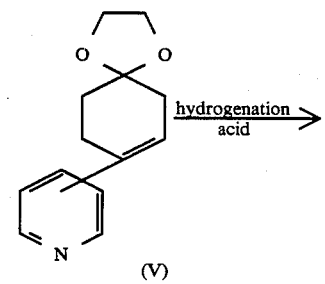

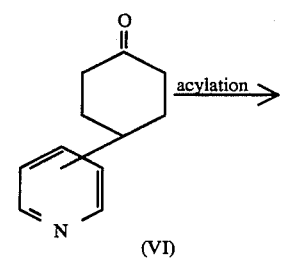

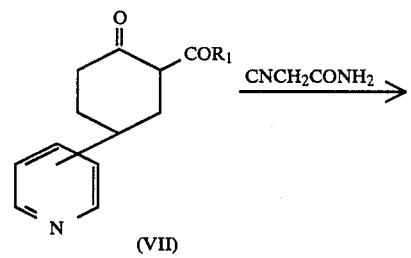

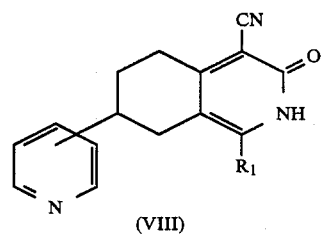

(2)

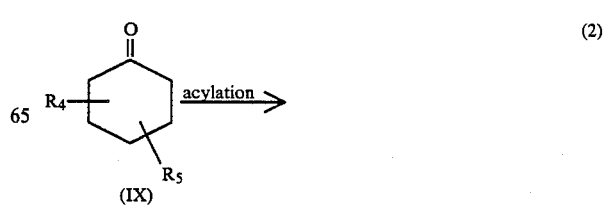

-continued

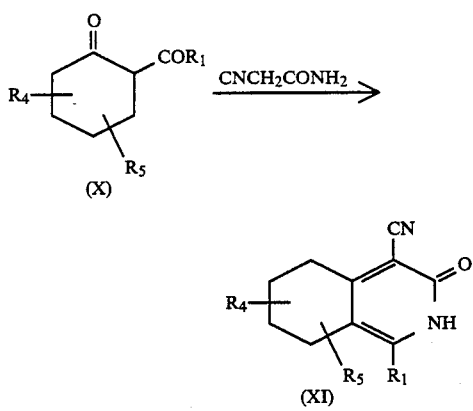

wherein $R_1$ is as defined above and $R_4$ and $R_5$ are the same as $R_2$ and $R_3$ defined above except a pyridyl group.

The compound (I) of the present invention wherein $R_2$ is a hydrogen atom and $R_3$ is a pyridyl group can be prepared by reaction (1). That is, monoethylene ketal (III) of 1,4-cyclohexanedione is condensed with 2-, 3- or 4-bromopyridine in the presence of n-butyllithium to give a compound (IV). This compound (IV) is reacted with thionyl chloride in pyridine to give a compound (V) which is subsequently hydrogenated in a mineral acid to give a compound (VI). The compound (VI) is acylated to give a compound (VII). Acetylation may be carried out with an appropriate acetylating agent such as acetylimidazole, acetic anhydride, an acetyl halide or an acetate in the presence of sodium alkoxide, sodium hydride, boron trifluoride/acetic acid, lithium diisopropylamide or zinc chloride. Alternately the compound (VI) may be converted into an enamine with pyrrolidine or the like followed by acetylation with acetic anhydride. The compound (VII) thus obtained is condensed with cyanoacetamide in the presence of a secondary amine such as piperidine or diethylamine or a sodium alkoxide in an alcohol such as methanol or ethanol to thereby give a compound (VIII). The compound (VIII) falls under the compound (I) of the present invention.

In reaction (2), a cyclohexanone derivative (IX) is acylated in the same manner as described in reaction (1) to give a compound (X), which is subsequently condensed with cyanoacetamide to thereby give a compound (XI). The obtained compound (XI) falls under the compound (I) of the present invention.

It is preferable to orally administer the compound of the present invention as a cardiotonic. However it may be administered parenterally, e.g., intravenously. It may be formulated into various types depending on the administration method. For example, the compound of the present invention or salts thereof may be administered as such or mixed with various nontoxic adjuvants such as pharmaceutically acceptable excipients, carriers, binders, stabilizers, diluents and flavors. These preparations may be formulated into tablets, capsules, granules, powder, syrup and elixir for oral administration and into injection for parenteral administration.

The dose of the compound of the present invention to a patient with heart failure should be determined by doctors depending on various factors such as the condition and age of the patient and the administration method. For example, 0.1 to 10 mg/kg body weight of the compound may be orally administered in a day though not necessarily limited thereto.

A novel isoquinoline derivative can be prepared according to the present invention. We have found that the novel isoquinoline derivative of the present invention is available as a cardiotonic and exhibits a low toxicity and a wide range of safety. The availability thereof as a cardiotonic can be confirmed by its effectiveness shown by a standard pharmacological test. For example, it can be regarded as useful when showing a significant reparative effect on cardiac function lowered by intravenous administration of propranslol under anesthesia.

To further illustrate the present invention, the following Examples and Test Examples will be given.

EXAMPLE 1:

4-cyano-2,3,5,6,7,8-hexahydro-1-methyl-3-oxo-7-(4-pyridyl)isoquinoline (1) 4-hydroxy-4-(4-pyridyl)cyclohexanone ethylene acetal 35 ml of ether was cooled to −78° C. and 20 ml of a 1.6 M solution of n-butyllithium in hexane was added thereto. To the obtained mixture, 5 g of 4-bromopyridine dissolved in 30 ml of ether was added. Then 5 g of 1,4-cyclohexanedione monoethylene acetal dissolved in 30 ml of tetrahydrofuran was further added thereto. After the completion of the reaction, the reaction mixture was poured into a saturated aqueous solution of ammonium chloride and purified by extracting with chloroform to give 5 g of 4-hydroxy-4-(4-pyridyl)cyclohexanone ethylene acetal. m.p.: 165.5°–167.5° C.

NMR$\delta_{TMS}^{COCl_3}$: 1.6 –2.2 (8H, m), 3.9 (1H, s), 4.00 (4H, S), 7.45 (2H, dd) and 8.44 (2H, dd).

(2) 4-(4-pyridyl)cyclohex-3-enone ethylene acetal 5 g of 4-hydroxy-4-(4-pyridyl)cyclohexanone ethylene acetal was dissolved in 40 ml of pyridine and 8 ml of thionyl chloride was added thereto at −10° C. The obtained mixture was stirred at 0° C. and poured onto ice and an excessive amount of an aqueous solution of sodium hydroxide was added thereto. After purifying the reaction mixture by extracting with methylene chloride, 4 g of 4-(4-pyridyl)cyclohex-3-enone ethylene acetal was obtained. m.p.: 67°–70° C. NMR$\delta_{TMS}^{CDCl_3}$: 1.86 (2H, t), 2.4–2.7 (4H, m), 4.04 (4H, s), 6.24 (1H, t), 7.28 (2H, d) and 8.52 (2H, d).

(3) 4-(4-pyridyl)cyclohexanone 4 g of 4-(4-pyridyl)cyclohex-3-enone ethylene acetal was dissolved in 70 ml of 0.5 N hydrochloric acid and 400 mg of 10% palladium/carbon was added thereto, to hydrogenate the starting compound at room temperature and atmospheric pressure. After the completion of the reaction, the catalyst was removed and the reaction mixture was made alkaline with an aqueous solution of sodium hydroxide and extracted with methylene chloride to thereby give 2.7 g of 4-(4-pyridyl)cyclohexanone. NMR$\delta_{TMS}^{CDCl_3}$: 1.7–2.3 (4H, m), 2.4–2.6 (4H, m), 2.8–3.2 (1H, M), 7.15 (2H, d) and 8.51 (2H, m).

(4) 2-acetyl-4-(4-pyridyl)cyclohexanone 3.2 ml of diisopropylamine was dissolved in 40 ml of tetrahydrofuran and 14.2 ml of a 1.6 M solution of n-butyllithium in hexane was added thereto at −20° C. A solution prepared by dissolving 2 g of 4-(4-pyridyl)cyclohexanone in 40 ml of tetrahydrofuran was further added thereto at −40° C. The obtained reaction mixture was cooled to −78° C. and 2.5 g of acetylimidazole dissolved in 40 ml of tetrahydrofuran was added thereto. After stirring at room temperature, the reaction mixture was poured onto ice water and washed with ether. The aqueous phase was saturated with ammonium chloride and extracted with methylene chloride to give 1.65 g of 2-acetyl-4-(4-pyridyl)cyclohexanone. NMR$\delta_{TMS}^{CDCl_3}$: 1.7–2.2 (3H, m), 2.16 (3H, s), 2.3–2.6 (3H, m), 2.6–2.9 (1H, m), 7.10 (2H, dd), 8.55 (2H, dd) and 15.7 (1H, s).

(5) 4-cyano-2,3,5,6,7,8-hexahydro-1-methyl-3-oxo-7-(4 pyridyl)isoquinoline 1.65 g of 2-acetyl-4-(4-pyridyl)cyclohexanone and 0.64 g of cyanoacetamide were dissolved in ethanol and a small amount of piperidine was added thereto. The obtained reaction mixture was heated under reflux for seven hours. After the completion of the reaction, crystals thus precipitated out were filtered to give 0.7 g of 4-cyano-2,3,5,6,7,8-hexahydro-1-methyl-3-oxo-7-(4-pyridyl)isoquinoline.
m.p.: 310° C. (decomp.). NMR$\delta_{TMS}^{DMSO-d_6}$: 1.7–2.1 (2H, m), 2.22 (3H, s), 2.3–2.7 (2H, m), 2.8–3.0 (3H, m), 7.35 (2H, dd) and 8.50 (2H, dd).

EXAMPLE 2

4-cyano-2,3,5,6,7,8-hexahydro-1-methyl-3-oxo-7-(2-pyridyl)isoquinoline (1) 4-hYdroxy-4-(2-pyridyl)cyclohexanone ethylene acetal The procedure of Example 1-(1) was followed except that 5 g of 2-bromopyridine was employed instead of the 4-bromopyridine to give 4.7 g of 4-hydroxy-4-(2-pyridyl)cyclohexanone ethylene acetal. NMR$\delta_{TMS}^{CDCl_3}$: 1.5−1.9 (4H, m), 1.9−2.4 (4H, m), 3.96 (4H, s), 7.2 (1H, dd), 7.4 (1H, d), 7.68 (1H, ddd) and 8.48 (1H, dd).

(2) 4-(2-pyridyl)cyclohex-3-enone ethylene acetal

The procedure of Example 1-(2) was followed except that 4.6 g of 4-hydroxy-4-(2-pyridyl)cyclohexanone ethylene acetal was employed to give 3.3 g of 4-(2-pyridyl)cyclohex-3-enone ethylene acetal. NMR$\delta_{TMS}^{CDCl_3}$: 1.92 (2H, t), 2.4–2.56 (2H, m), 2.64–2.82 (2H, m), 3.96 (4H, s), 6.44–6.60 (1H, m), 7.12 (1H, dd), 7.36 (1H, d), 7.58 (1H, ddd) and 8 52 (1H, dd).

(3) 4-(2-pyridyl)cyclohexanone

The procedure of Example 1-(3) was followed except that 3.3 g of 4-(2-pyridyl)cyclohex-3-enone ethylene acetal was employed to give 2.2 g of 4-(2-pyridyl)cyclohexanone. NMR$\delta_{TMS}^{CDCl_3}$: 1.8–2.6 (8H, m), 3.0–3.32 (1H, m), 7.0–7.3 (2H, m), 7.62 (1H, ddd) and 8.48 (1H, dd).

(4) 2 acetyl-4-(2-pyridyl)cyclohexanone

The procedure of Example 1-(4) was followed except that 1.9 g of 4-(2-pyridyl)cyclohexanone was employed to give 2-acetyl-4-(2-pyridyl)cyclohexanone. The total amount of this crude compound was subjected to the subsequent step as such.

(5) 4-cyano-2,3,5,6,7,8-hexahydro-1-methyl-3-oxo-7-(2-pyridyl)isoquinoline

The total amount of the crude 2-acetyl-4-(2-pyridyl)cyclohexanone prepared in (4) was treated in the same manner as described in Example 1-(5) to give 0.76 g of 4-cyano-2,3,5,6,7,8-hexahydro-1-methyl-3-oxo-7-(2-pyridyl)isoquinoline. m.p.>300° C. NMR$\delta_{TMS}^{DMSO-d_6}$:1.8–2.2 (2H, m), 2.24 (3H, s), 2.4–2.6 (2H, m), 2.8–3.1 (3H, m), 7.2–7.5 (2H, m), 7.76 (1H, m), 8.54 (1H, m) and 12.3 (1H, s).

EXAMPLE 3

4-cyano-2,3,5,6,7,8-hexahydro-1-methyl-3-oxo-7-(3-pyridyl)isoquinoline (1) 4-hydroxy-4-(3-pyridyl)cyclohexanone ethylene acetal The procedure of Example 1-(1) was followed except that 5 g of 3-bromopyridine was employed instead of the 4 bromopyridine to give 3.5 g of 4-hydroxy-4-(3-pyridyl)cyclohexanone ethylene acetal. NMR$\delta_{TMS}^{CDCl_3}$: 1.56–2.52 (8H, m), 3.3 (1H s), 3.94 (4H, s), 7.24 (1H, dd), 7.84 (1H, ddd), 8.36 (1H, dd) and 8.68 (1H, d).

(2) 4-(3-pyridyl)cyclohex-3-enone ethylene acetal

The procedure of Example 1-(2) was followed except that 3.5 g of 4-hydroxy-4-(3-pyridyl) cyclohexanone ethylene acetal was employed to give 2.6 g of 4-(3-pyridyl)cyclohex-3-enone ethylene acetal. NMR$\delta_{TMS}^{CDCl_3}$: 1.82 (2H, t), 2.4–2.52 (2H, m). 2.52–2.76 (2H, m), 3.98 (4H, s). 59.96–6.08 (1H, m), 7.24 (1H, dd), 7.64 (1H, ddd), 8.44 (1H, dd) and 8.64 (1H, d).

(3) 4-(3-pyridyl)cyclohexanone

The procedure of Example 1-(3) was followed except that 2.6 g of 4-(3-pyridyl)cyclohex-3-enone ethylene acetal was employed to give 4-(3-pyridyl)-cyclohexanone. NMR$\delta_{TMS}^{CDCl_3}$ : 1.7–2.7 (8H, m), 2.92–3.3 (1H, m), 7.44 (1H, dd), 7.54 (1H, ddd), 8.44 (1H, dd) and 8.5 (1H, d).

(4) 2-acetyl-4-(3-pyridyl)cyclohexanone

The procedure of Example 1-(4) was followed except that 4-(3-pyridyl)cyclohexanone was employed to give 2-acetyl-4-(3-pyridyl)cyclohexanone. The total amount of this crude compound was subjected to the subsequent step as such.

(5) 4-cyano-2,3,5,6,7,8-hexahydro-1-methyl-3-oxo-7-(3-pyridyl)isoquinoline

The total amount of the 2-acetyl-4-(3-pyridyl)cyclohexanone prepared in (4) was treated in the same manner as described in Example 1-(5) to give 0.57 g of 4-cyano-2,3,5,6,7,8-hexahydro-1-methyl-3-oxo-7-(3-pyridyl)isoquinoline. m.p. >300° C. NMR$\delta_{TMS}^{DMSO-d_6}$: 1.7 (2H, m), 2.22 (3H, s), 2.3–2.76 (2H, m), 2.76–3.1 (3H, m), 7.36 (1H, dd), 7.72 (1H, ddd), 8.42 (1H, dd) and 8.52 (1H, d).

EXAMPLE 4

4-cyano-2,3,5,6,7,8-hexahydro-7-methoxy-1-methyl-3-oxoisoquinoline (1) 2-acetyl-4-methoxycyclohexanone 1.12 g of 60% sodium hydride was added to 2.5 g of ethyl acetate and 1.78 g of a benzene solution of 4-methoxycyclohexanone was added thereto. After reacting at 40° C. for three hours, methanol was added to thereby decompose excessive sodium hydride and the reaction mixture was poured into water, neutralized with hydrochloric acid and extracted with ether to give 1.02 g of 2-acetyl4-methoxycyclohexanone. $NMR\delta_{TMS}^{CCl_4}$: 2.06 (3H, s). 1.7-2.5 (8H, s), 3.28 (3H, s), 3.4 (1H, m) and 15.9 (1H, s).

(2) 4-cyano-2,3,5,6,7,8-hexahydro-7-methoxy-1-methyl-3-oxo-isoquinoline 1.02 g of 2-acetyl-4-methoxycyclohexanone and 0.462 g of cyanoacetamide were mixed with 5 ml of ethanol and a small amount of piperidine was added thereto. The obtained reaction mixture was heated under reflux for two hours. The crystals thus precipitated were filtered and recrystallized from methanol to give 0.42 g of 4-cyano-2,3,5,6,7,8-hexahydro-7-methoxy-1-methyl-3-oxoisoquinoline. m.p. 257°-259° C. $NMR_{TMS}^{CF_3COOH}$: 2.25 (2H, m), 2.57 (3H, s), 2.97 (2H, m), 3.20 (2H, m), 3.66 (3H, s) and 4.16 (1H, m).

EXAMPLE 5

4-cyano-1,7-dimethyl-2,3,5,6,7,8hexahydro-3-oxoisoquinoline (1) 2-acetyl-4-methylcyclohexanone 24 g of 40% boron trifluoride/acetic acid complex was cooled with ice and a mixture of 5.6 g of 4-methylcyclohexanone and acetic anhydride was added dropwise thereto. After stirring at room temperature for four hours, approximately 50 ml of a saturated aqueous solution of sodium acetate was added thereto and the obtained reaction mixture was heated under reflux for one hour. After cooling, the reaction mixture was extracted with ether, washed with an aqueous solution of sodium hydrogencarbonate and water and dried, and ether was distilled off. The total amount of the crude 2-acetyl-4-methylcyclohexanone thus obtained was subjected to the subsequent step as such.

(2) 4-cyano-1,7-dimethyl-2,3,5,6,7,8-hexahydro-3-oxoisoquinoline

To the total amount of the crude 2-acetyl-4methylcyclohexanone prepared in (1), 35 ml of ethanol, 3.36 g of cyanoacetamide and a small amount of piperidine were added and the obtained reaction mixture was heated under reflux for four hours. The crystals thus precipitated were filtered and recrystallized from a mixture of methanol and water to give 4.22 g of 4-cyano-1,7-dimethyl-2,3,5,6,7,8hexahydro-3-oxoisoquinoline. m.p. >290° C. $NMR\delta_{TMS}^{CF_3COOH}$: 1.23 (3H, d), 2.60 (3H, s) and 1.8-3.3 (7H,m).

EXAMPLE 6

4-cyano-2,3,5,6,7,8-hexahydro-1-methyl-3-oxo-7-phenylisoquinoline (1) 2-acetyl-4-phenylcyclohexanone 5.5 g of boron trifuloride/acetic acid complex was cooled with ice and a benzene solution of 2 g of 4-phenylcyclohexanone and 2.35 g of acetic anhydride was added thereto dropwise. After stirring under ice cooling for 30 min and then at room temperature for four hours, 10 ml of a saturated aqueous solution of ammonium acetate was added thereto and the obtained reaction mixture was stirred at 80° C. for 1.5 hour and purified by extracting with ether to give 1.77 g of 2-acetyl-4phenylcyclohexanone. m.p.: 53-54° C. $NMR\delta_{TMS}^{DMSO-d_6}$: 1.90 (3H, m), 2.10 (3H, s), 2.50 (6H, m), 7.26 (5H, s) and 10.58 (1H, s).

(2) 4 cyano-2,3,5,6,7,8-hexahydro-1-methyl-3-oxo-7-phenylisoquinoline 1.68 g of 2-acetyl-4-phenylcyclohexanone, 0.73 g of cyanoacetamide and a small amount of piperidine were mixed with 10 ml of ethanol and the obtained reaction mixture was heated under reflux for two hours. After cooling, the precipitated crystals were filtered and purified to give 1.5 g of 4-cyano-2,3,5,6,7,8-hexahydro-1-methyl- 3-oxo-7-phenylisoquinoline. m.p. >290° C. $NMR\delta_{TMS}^{DMSO-d_6}$: 1.90 (3H, m), 2.20 (3H, s), 2.80 (4H, m), 7.28 (5H, s) and 12.14 (1H, s).

EXAMPLE 7

4-cyano-2,3,5,6,7,8-hexahydro-1-methoxymethyl-7-methyl-3-oxoisoquinoline (1) 2-methoxyacetyl-4-methylcyclohexanone 2.5 g of 60% sodium hydride was suspended in 50 ml of benzene and a mixture of 5.6 g of 4methylcyclohexanone and 5.4 g of methoxyethyl acetate was added dropwise thereto under cooling. After stirring at room temperature for two hours, 20 ml of water was added and the pH value of the reaction mixture was adjusted to 3 with concentrated hydrochloric acid. After removing the benzene phase the aqueous phase was extracted with ether. The benzene solution and the ether solution were combined, washed with water, dried and concentrated to give 7.4 g of crude 2-methoxyacetyl4-methylcyclohexanone. This crude product was subjected to the subsequent step.

(2) 4-cyano 2,3,5,6,7,8-hexahydro-1-methoxymethyl-7-methyl-3-oxoisoquinoline 3.7 g of the crude 2-methoxyacetyl-4-methylcyclohexanone, 1.68 g of cyanoacetamide and 1 ml of piperidine were mixed with 50 ml of ethanol and the obtained reaction mixture was heated under reflux for four hours. The crystals thus formed were filtered and purified to give 1.5 g of 4-cyano-2,3,5,6,7,8-hexahydro-1-methoxymethyl-7-methyl-3-oxoisoquinoline. m.p.: 205°-208° C. $NMR\delta_{TMS}^{DMSO-d_6}$:1.01 (3H, d), 1.2-2.0 (4H, m), 2.5-2.6 (1H, m), 2.7-2.9 (2H, m), 3.28 (3H, s), 4.32 (2H, s) and 11.86 (1H, s).

Table 1 shows other compounds prepared in a similar manner to those described in Examples 1 to 7.

TABLE 1

| No. | R₁ | R₂*¹ | R₃*¹ | m.p. (°C.) | NMR (δ)*² |
|---|---|---|---|---|---|
| 8 | CH₃ | 5-CH₃ | H | 267 (dec.) | 1.23 (3H, d), 1.5-2.4 (7H, m), 2.18 (3H, S) |
| 9 | CH₃ | 6-CH₃ | H | >290 | 1.22 (3H, d), 1.3-1.7 (1H, m), 1.7-2.3 (2H, m), 2.57 (3H, s), 2.4-2.9 (3H, m) |
| 10 | CH₃ | 8-CH₃ | H | >300 | 1.07 (3H, d), 1.6-1.9 (4H, m), 2.28 (3H, S), 2.6-3.0 (3H, m), 12.16 (1H, S) |
| 11 | CH₃ | 7-C₂H₅ | H | 288 (dec.) | 0.96 (3H, t), 1.2-1.6 (4H, m), 1.7-2.1 (2H, m), 2.24 (3H, S), 2.6-2.9 (3H, m), 12.2 (1H, S) |
| 12 | CH₃ | 7-cyclohexyl | H | 250-252 | 1.0-2.80 (18H, S), 2.10 (3H, S), 12.0 (1H, S) |
| 13 | CH₃ | 7-(3,4-dimethoxyphenyl) | H | 293 (dec.) | 2.39 (3H, S), 2.0-3.2 (7H, m), 3.84 (3H, S), 3.86 (3H, S), 6.7-6.9 (3H, m), 14.0 (1H, S) |
| 14 | CH₃ | 7=O | H | 260 (dec.) | 2.23 (3H, S), 2.48 (2H, dd), 3.08 (2H, dd), 3.30 (2H, S), 12.70 (1H, S) |
| 15 | CH₃ | 8=O | H | 218 (dec.) | 2.0-2.2 (2H, m), 2.62 (2H, dd), 2.82 (3H, S), 3.08 (2H, dd), 13.55 (1H, S), |
| 16 | CH₃ | 7-OCH₃ | 7-OCH₃ | 280 (dec.) | 1.92 (2H, dd), 2.24 (3H, S), 2.58 (2H, S), 2.72 (2H, dd), 3.16 (6H, S), 12.65 (1H, S) |
| 17 | CH₃ | 7-OCH₃ | 8=O | 245 (dec.) | 1.9-2.3 (2H, m), 2.62 (3H, S), 3.50 (2H, dd), 3.28 (3H, S), 3.86 (1H, dd), 12.40 (1H, S) |

*¹Each figure represents the position of a substituent.
*²Solvent: DMSO—d6: No. 8, 10, 11, 12, 14, 16, 17
CDCl₃: 13, 15, CF₃COOH: 9

Test Example 1

Female and male adult mongrel dogs of 8 to 12 kg in body weight were anesthetized by intravenously administering 30 mg/kg of sodium pentobarbital. A catheter tonosenser was inserted from the right carotid artery of a dog into the left ventricle to determine the intraventricular pressure. The primary differential of the intra-left-ventricular pressure was calculated with the use of a differential meter, thus determining the maximum variation of the intra-left-ventricular pressure (LV dp/dt max). A polyethylene cannula connected with a pressure transducer was inserted into the right femoral artery of the dog to thereby determine the constitutional blood pressure. The heart rate was determined from the pulse wave with a cardiometer. The first administration was carried out via the right femoral artery while continuous administration was carried out from the left femoral vein. Each parameter was recorded on a thermorecorder at the same time.

The dog was brought into a stable state of cardiac insufficiency by intravenous administration of 4 mg/kg of propranolol and continuous intravenous administration of 0.1 mg/kg/min of the same. That is, the blood pressure, the heart rate and the intra-left-ventricular pressure of the dog were somewhat decreased and the LV dp/dt thereof was significantly decreased. The dose of a test compound capable of recovering the decreased LV dp/dt max to the level prior to the administration of propranolol was determined and referred to as the effective dose ($ED_{100}$). Changes in the blood pressure and heart rate at the $ED_{100}$ were compared with those at the administration of propranolol. Table 2 shows the result.

TABLE 2

| No.*¹ | $ED_{100}$ (mg/kg, i.v.) | Blood pressure (%) | Heart rate (%) |
|---|---|---|---|
| 1 | 0.1 | −8.7 | 27.6 |
| 2 | 0.1 | −5.1 | 18.7 |
| 3 | 0.1 | 11.3 | 26.1 |
| 4 | 1.0 | −16.7 | 22.1 |
| 5 | 0.3 | −24.6 | 25.5 |
| 6 | 0.1 | 4.0 | 11.0 |
| 7 | 3.0 | −11.8 | 18.8 |
| 8 | 1.0 | −6.7 | 20.2 |
| 9 | 1.0 | −11.9 | 24.8 |
| 10 | 3.0 | −28.3 | 31.1 |
| 11 | 0.3 | −10.8 | 24.5 |
| 12 | 0.1 | −16.8 | 13.6 |
| 13 | 1.0 | −21.6 | 34.4 |
| 14 | 3.0 | −18.5 | 26.7 |
| 15 | 3.0 | −17.1 | 21.6 |
| 16 | 0.3 | −10.1 | 31.4 |
| 17 | 3.0 | −20.7 | 24.2 |

*¹Nos. 1 to 7 represent the above Examples, while Nos. 8 to 17 correspond to those shown in Table 1.

Test Example 2

Acute toxicity test

Male ddy mice aged five weeks fasting for 18 hours were classified into groups each consisting of five animals. A test compound dissolved or suspended in a physiological saline solution was orally administered to each group. After the administration, the animals were observed for seven days to determine $LD_{50}$. It was found that the $LD_{50}$ of the active ingredient of the pharmaceutical of the present invention was not lower than 400 mg/kg.

We claim:
 1. An isoquinoline derivative of the formula:

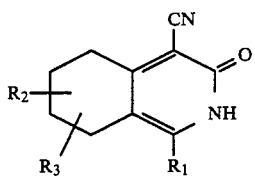

wherein $R_1$ is a methyl or a methoxymethyl group and $R_2$ and $R_3$ are each a hydrogen atom or a methyl, ethyl, methoxy, a cyclohexyl, a phenyl, 3,4-dimethoxy phenyl, a pyridyl or an oxo (=O) group;

and therapeutically acceptable salts thereof.

2. A compound as set forth in claim 1 which is 4-cyano-2,3,5,6,7,8-hexahydro-1-methyl-3-oxo-7(4-pyridyl)isoquinoline.

3. A compound as set forth in claim 1 which is 4-cyano-2,3,5,6,7,8-hexahydro-1-methyl-3-oxo-7(2-pyridyl)isoquinoline.

4. A compound as set forth in claim 1 which is 4-cyano-2,3,5,6,7,8-hexahydro-7-methoxy-1-methyl-3-oxoisoquinoline.

* * * * *